United States Patent
Malina et al.

(10) Patent No.: US 10,490,057 B1
(45) Date of Patent: Nov. 26, 2019

(54) HYGIENIC SENSOR DEVICE, SYSTEM, AND METHOD FOR MONITORING HYGIENIC DISPENSER USAGE AND COMPLIANCE

(71) Applicant: SWIPESENSE, INC., Chicago, IL (US)

(72) Inventors: Yuri F. Malina, Chicago, IL (US); Thomas F. Racke, Highland Park, IL (US); Harikrishna K. Rajabather, Dallas, TX (US); Horace Y. Wang, Chicago, IL (US); John R. Peck, Pleasanton, CA (US)

(73) Assignee: SwipeSense, Inc., Chicago, IL (US)

( * ) Notice: Subject to any disclaimer, the term of this patent is extended or adjusted under 35 U.S.C. 154(b) by 0 days.

(21) Appl. No.: 15/867,402

(22) Filed: Jan. 10, 2018

Related U.S. Application Data

(60) Provisional application No. 62/445,198, filed on Jan. 11, 2017.

(51) Int. Cl.
  *G08B 21/24* (2006.01)
  *A47K 5/12* (2006.01)

(52) U.S. Cl.
  CPC .......... *G08B 21/245* (2013.01); *A47K 5/1217* (2013.01)

(58) Field of Classification Search
  CPC .......................... G08B 21/245; A47K 5/1217
  See application file for complete search history.

(56) References Cited

U.S. PATENT DOCUMENTS

| | | | |
|---|---|---|---|
| 6,542,568 B1 | 4/2003 | Howes et al. | |
| 6,731,209 B2 | 5/2004 | Wadlow et al. | |
| 7,659,824 B2 | 2/2010 | Prodanovich et al. | |
| 7,682,464 B2 | 3/2010 | Glenn et al. | |
| 7,783,380 B2 | 8/2010 | York et al. | |
| 8,154,412 B2 | 4/2012 | Verdiramo | |
| 8,400,309 B2 | 3/2013 | Glenn et al. | |
| 8,502,680 B2 | 8/2013 | Tokhtuev et al. | |
| 2002/0175182 A1 | 11/2002 | Matthews | |
| 2005/0134465 A1 | 6/2005 | Rice et al. | |
| 2005/0269362 A1* | 12/2005 | Guerrero | A61L 2/18 222/148 |
| 2007/0000941 A1 | 1/2007 | Hadden et al. | |
| 2008/0109956 A1 | 5/2008 | Bayley et al. | |

(Continued)

*Primary Examiner* — Nader Bolourchi
(74) *Attorney, Agent, or Firm* — Renaissance IP Law Group, LLP; David A. Crowther

(57) ABSTRACT

The disclosed device, system, and method can be used for monitoring hygienic dispenser usage and compliance. A hygienic dispenser dispenses a hygienic substance such as sanitizer, soap, a glove, or the like. A hygienic sensor adapter device is proximately disposed to the hygienic dispenser. The hygienic sensor adapter device detects a presence of a human hand within an activation area of the dispenser. The hygienic sensor adapter device includes a sensor to detect badges worn by corresponding human subjects. A remote cloud-based computer server can determine a particular human subject from among the human subjects to which the human hand belongs. Accordingly, the hygienic sensor adapter device is able to monitor the activations of all models of hand hygiene dispensers with little to no configuration or modification. The hygienic sensor adapter device rejects false triggers, captures every dispenser activation, and identifies the subject responsible for the dispenser activation.

16 Claims, 7 Drawing Sheets

(56) References Cited

U.S. PATENT DOCUMENTS

| | | | |
|---|---|---|---|
| 2009/0051545 A1 | 2/2009 | Koblasz | |
| 2010/0134296 A1* | 6/2010 | Hwang | A47K 5/1217 340/573.1 |
| 2010/0315244 A1* | 12/2010 | Tokhtuev | G08B 21/245 340/603 |
| 2011/0169646 A1* | 7/2011 | Raichman | G08B 21/245 340/573.1 |
| 2013/0262034 A1* | 10/2013 | Iseri | G08B 21/245 702/187 |

\* cited by examiner

US 10,490,057 B1

HYGIENIC SENSOR DEVICE, SYSTEM, AND METHOD FOR MONITORING HYGIENIC DISPENSER USAGE AND COMPLIANCE

RELATED APPLICATION DATA

This application claims the benefit of U.S. Provisional Patent Application Ser. No. 62/445,198, filed on Jan. 11, 2017, which is hereby incorporated by reference.

TECHNICAL FIELD

This application pertains to sensing devices and methods, and more particularly, to proximity sensing for monitoring hygienic device usage.

BACKGROUND

Every year millions of medical patients around the world acquire infections during their hospitalization. The World Health Organization (WHO) and the Center for Disease Control and Prevention (CDC) recognize lack of hand hygiene amongst healthcare workers as the primary cause of hospital-acquired infections. As a result of this, medical facilities around the world attempt to measure the hand hygiene compliance of their staff. Other industries such as the food, education and transportation sectors also attempt to measure hygiene dispenser usage.

Most industries currently measure hand hygiene through inaccurate means. Such convention means include volumetric consumption over time or manual observation. The conventional techniques and devices all have drawbacks: some operate only with specific dispenser models, others require gross modifications in user workflow, others are highly inaccurate, while others provide no means for identifying the user responsible for dispenser use. While some electronic methods exist to attribute dispenser usage to individuals, these methods often rely on limited information such as relying solely on the proximity of a badge to determine attribution, leading to reduced accuracy. The compliance problems are further complicated by the many different soap and sanitizer dispenser models available on the market, none of which have the capability of providing true compliance with regulations. Accordingly, a need remains for improved methods, systems, and devices to monitor any type of dispenser use and accurately attribute usage to individuals, in order to increase hand hygiene and reduce hospital-acquired infections. Embodiments of the inventive concept address these and other limitations in the prior art.

Figure 1:
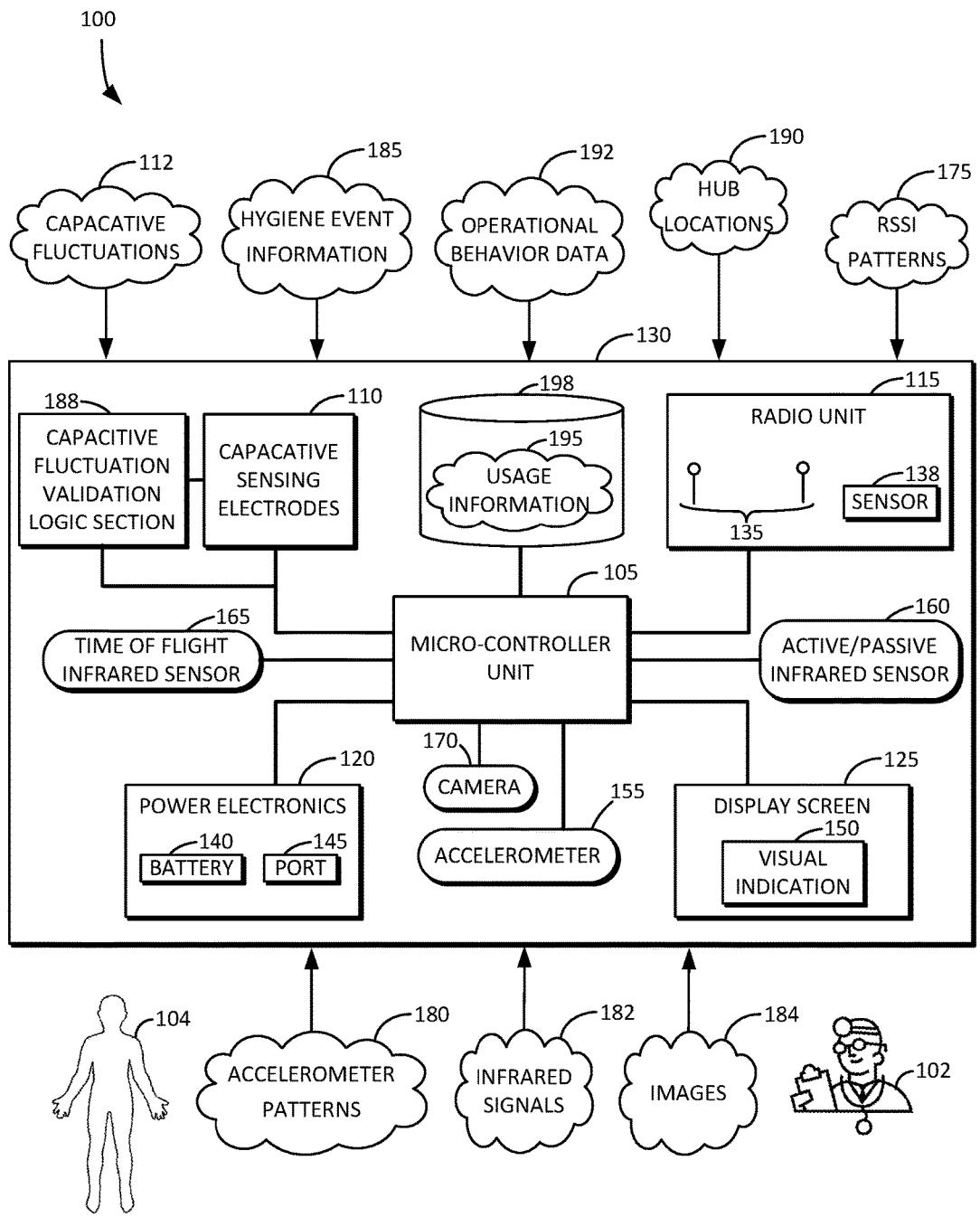
FIG. 1 illustrates a block diagram of an example hygienic sensor adapter device in accordance with various embodiments of the present inventive concept.

The foregoing and other features of the inventive concept will become more readily apparent from the following detailed description, which proceeds with reference to the accompanying drawings.

DETAILED DESCRIPTION OF THE EMBODIMENTS

Reference will now be made in detail to embodiments of the inventive concept, examples of which are illustrated in the accompanying drawings. The accompanying drawings are not necessarily drawn to scale. In the following detailed description, numerous specific details are set forth to enable a thorough understanding of the inventive concept. It should be understood, however, that persons having ordinary skill in the art may practice the inventive concept without these specific details. In other instances, well-known methods, procedures, components, circuits, and networks have not been described in detail so as not to unnecessarily obscure aspects of the embodiments.

It will be understood that, although the terms first, second, etc. may be used herein to describe various elements, these elements should not be limited by these terms. These terms are only used to distinguish one element from another. For example, a first dispenser could be termed a second dispenser, and, similarly, a second dispenser could be termed a first dispenser, without departing from the scope of the inventive concept.

It will be understood that when an element or layer is referred to as being "on," "coupled to," or "connected to" another element or layer, it can be directly on, directly coupled to or directly connected to the other element or layer, or intervening elements or layers may be present. In contrast, when an element is referred to as being "directly on," "directly coupled to," or "directly connected to" another element or layer, there are no intervening elements or layers present. Like numbers refer to like elements throughout. As used herein, the term "and/or" includes any and all combinations of one or more of the associated listed items.

The terminology used in the description of the inventive concept herein is for the purpose of describing particular embodiments only and is not intended to be limiting of the inventive concept. As used in the description of the inventive concept and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the present inventive concept provide a hygienic sensor adapter device that is able to monitor the activations of all models of hand hygiene dispensers with little to no configuration or modification. The hygienic sensor device disclosed herein can detect a dispenser use without requiring an additional user step or change in workflow. In addition, the hygienic sensor adapter device has a high degree of accuracy, able to reject false triggers, and capture every activation. The disclosed hygienic sensor device is able to identify the subject responsible for the activation of the dispenser.

In some embodiments, the hygienic sensor device disclosed herein can detect that a human being has used a given dispenser to eject fluid. There are a multitude of dispensers that can be used to eject hand hygiene fluids. However due to the difference in mechanical sizes, different environments, and the like, the ability to detect a human subject using the dispenser is complicated. The disclosed hygienic sensor device has the ability to detect a valid hand hygiene usage (i.e., that a hygienic dispenser is being activated and dispense fluid is being received). Moreover, the disclosed hygienic sensor device has the ability to detect the specific human subject that used the dispenser.

More specifically, the disclosed hygienic sensor device can detect when a human hand is used to activate a dispenser using one or more of a variety of different sensors such as capacitive proximity sensing, infrared, video, accelerometer, or the like. The hygienic sensor device disclosed herein can include built-in logic, which can pattern-match a hand signal compared to a signal otherwise caused by environmental conditions. The disclosed hygienic sensor device need not be directly connected to the dispenser, but rather, only needs to be located proximate to where the subject's hands are located when activating the dispenser. In some embodiments, the disclosed hygienic sensor device is directly connected to or otherwise included within the dispenser. The dispenser can dispense soap, alcohol, lotion, a glove, a medication, or the like.

In some embodiments, the disclosed hygienic sensor device is shaped like a drip guard and/or drip tray, serving to replace the existing drip trays common on most modern soap and sanitizer dispensers. In some embodiments, the disclosed hygienic sensor device has any suitable shape to allow it's sensors to carry out the necessary measurements required to detect hygienic dispenser activation. In some embodiments, after the detection, the disclosed hygienic sensor device can use RF signal strength to determine nearest badges or devices. An antenna associated with the hygienic sensor device can give the hygienic sensor device directionality towards the subject using the dispenser. The disclosed hygienic sensor device can include the antenna. Based on apriori data and the prior and following motion patterns of the subject and/or of other users identified in proximity, the hygienic sensor device and/or the cloud can determine which user is most likely to have used the device at a given time.

FIG. 1 illustrates a block diagram of an example hygienic sensor adapter device 100 in accordance with various embodiments of the present inventive concept. The hygienic sensor adapter device 100 can include a micro-controller unit 105, one or more capacitive sensing electrodes 110, a capacitive fluctuation validation logic section 188, a radio unit 115, power electronics 120, and a display screen 125. In some embodiments, a housing 130 encases the various components of the hygienic sensor adapter device 100 disclosed herein. The housing 130 can be a plastic encasement, for example. In some embodiments, the housing 130 may include or otherwise be shaped as a drip-guard or drip-tray, as further described below.

The micro-controller unit 105 can be coupled to each of the other components and can process information received from such components, and control the overall operation of the hygienic sensor adapter device 100. The capacitive sensing electrodes 110 can detect capacitive fluctuations 112 associated with a hand signal near the hygienic sensor adapter device 100. The capacitive fluctuation validation logic section 188 can receive and interpret the capacitive fluctuations 112, and determine whether the capacitive fluctuations 112 indicate a valid hand signal. While generally referred to herein as capacitive sensing electrodes 110, it will be understood that other suitable kinds of sensors can be used.

The radio unit 115 can include one or more antennas 135. The radio unit 115 can detect nearby badges, as described below using some form of wireless communication such as Bluetooth®, Bluetooth LE®, Zigbee®, near-field communication (NFC), or the like. In some embodiments, the radio unit 115 includes a sensor 138. The one or more antennas 135 and/or the sensor 138 can be used to transmit and/or receive wireless signals. In some embodiments, the radio unit 115 only includes the one or more antennas 135 and not the sensor 138. In some embodiments, the radio unit 115 only includes the sensor 138 and not the one or more antennas 135. Alternatively or in addition, the radio unit 115 can wirelessly transmit information to a network such as the Internet. For example, the radio unit 115 can wirelessly transmit badge identifiers, as explained in further detail below. The power electronics 120 can include one or more batteries 140, a power port 145, or both, and can facilitate the provision of power to the other components of the hygienic sensor adapter device 100.

The display screen 125 can provide a visual indication 150. The visual indication 150 can include visual information such as letters, numbers, graphs, icons, or the like, about the status or operation of the hygienic sensor adapter device 100 to a user. The hygienic sensor adapter device 100 can detect specific hand movement patterns of a subject (e.g., 102 or 104), in any activation scenario. The term "subject" as used herein refers to a human individual such as a healthcare provider 102 or a patient 104. The healthcare provider 102 can include a doctor, a nurse, or other healthcare practitioner.

In some embodiments, the hygienic sensor adapter device 100 can include an accelerometer 155 that is configured to sense subtle movements of the hygienic sensor adapter device 100. Other sensors can be included or otherwise used such as an active or passive infrared sensor 160, a time of flight infrared sensor 165, a visible light camera 170, or the like. For example, two or more different kinds of sensors (e.g., 155, 160, 165, and/or 170) can be included in the housing 130 or otherwise used by the hygienic sensor adapter device 100.

Figure 2A:
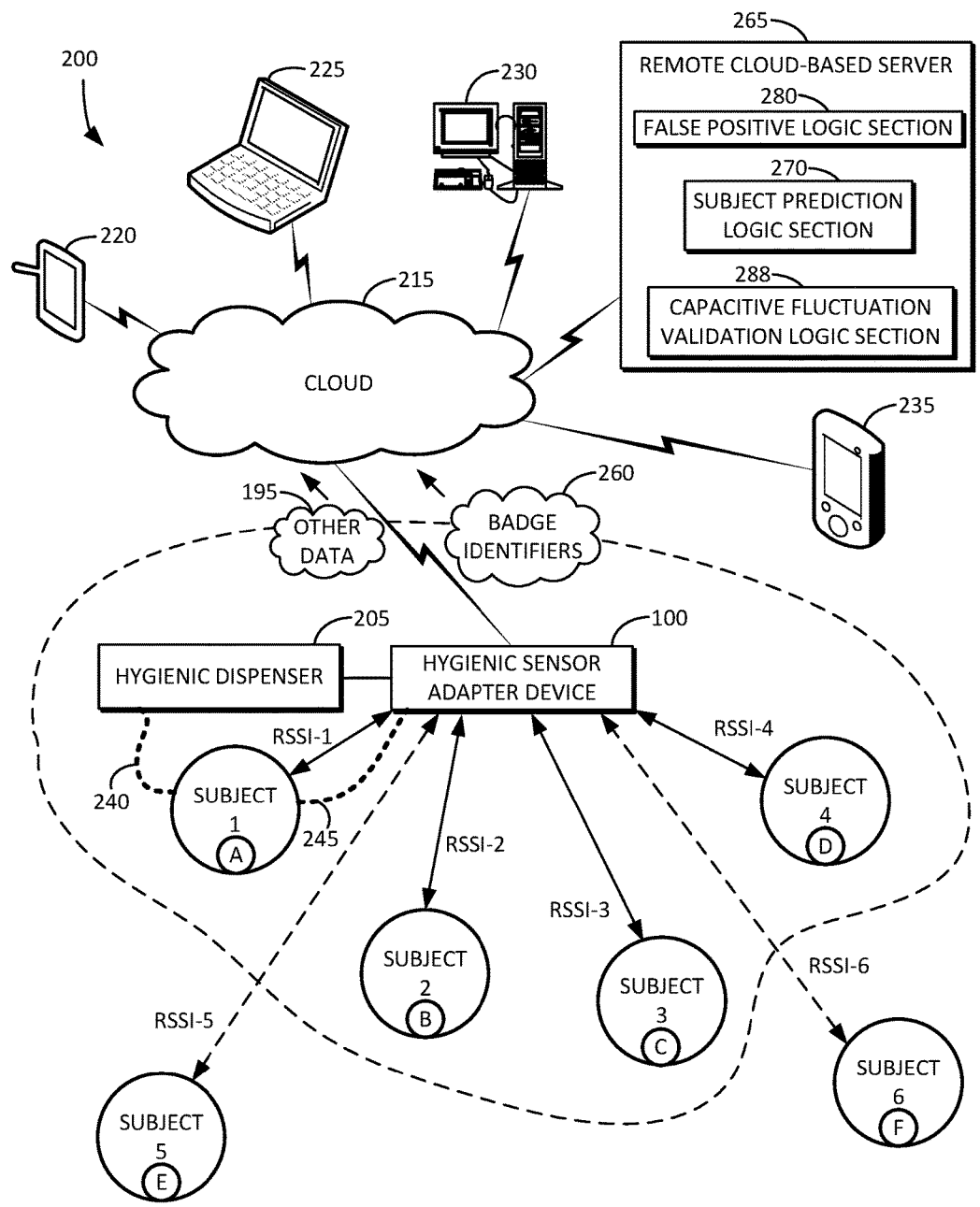
FIG. 2A illustrates a block diagram of an example hygienic sensor system including a hygienic sensor adapter device, a hygienic dispenser, and multiple subjects in varying proximity to the dispenser in accordance with various embodiments of the present inventive concept.
Figure 2B:
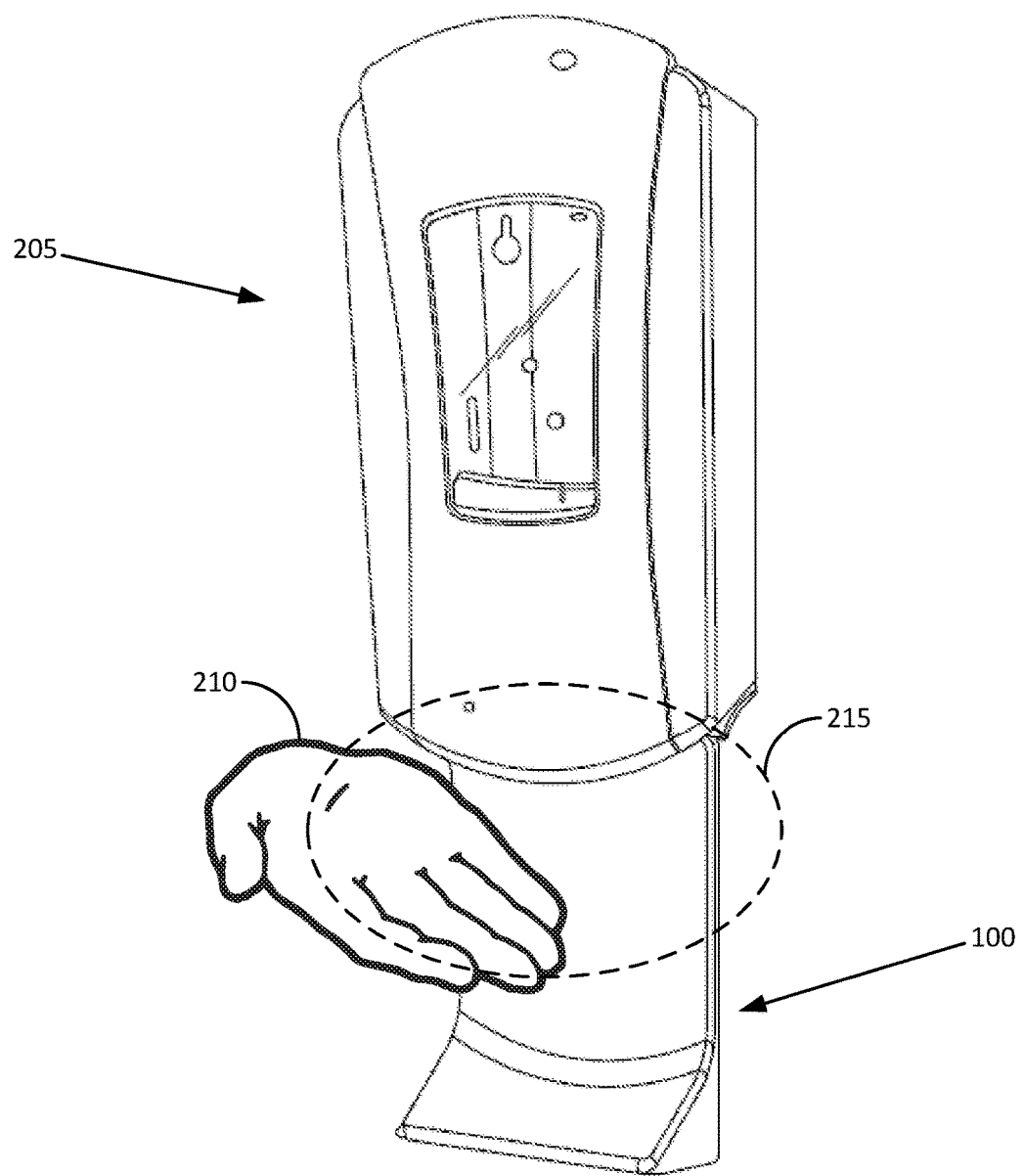
FIG. 2B illustrates an example hygienic sensor adapter device and a hygienic dispenser in accordance with various embodiments of the present inventive concept.

FIG. 2A illustrates a block diagram of an example hygienic sensor system 200 including the hygienic sensor adapter device 100 of FIG. 1, a hygienic dispenser 205, and multiple subjects (e.g., subject 1 through 6) in varying proximity to the hygienic sensor adapter device 100 and the hygienic dispenser 205 in accordance with various embodiments of the present inventive concept. FIG. 2B illustrates an example hygienic sensor adapter device 100 and a hygienic dispenser 205 in accordance with various embodiments of the present inventive concept. Reference is now made to FIGS. 1, 2A, and 2B.

Data from the multiple sensors (e.g., 155, 160, 165, and/or 170) can provide a more accurate determination with respect to the presence of a human hand 210 in proximity to the hygienic sensor adapter device 100. Received signal strength information (RSSI) patterns 175, accelerometer patterns 180, infrared signals 182, one or more images 184, hygiene event information 185, operational behavior data 192, hub locations 190, capacitive fluctuations 112, or the like, can be gathered and analyzed to increase accuracy of room-level positioning of subjects (e.g., 102 or 104) to discern usage information 195 about a hygienic dispenser (e.g., 205), and to associate the subjects (e.g., 102 or 104) with the usage patterns 195. The usage information 195 including the usage patterns can be stored, for example, in a storage device 198 within the hygienic sensor adapter device 100. The hygiene event information 185 can include instances in which a subject (e.g., 102 or 104) used or was suspected to use the hygienic dispenser 205. The hygiene event information 185 can be used to reward the subject for consistent use of the hygienic dispenser 205, or to otherwise penalize the subject for inconsistent use of the hygienic dispenser 205.

The operational behavior data 192 can include operational behavior associated with the hygienic dispenser (e.g., 205), such as whether the hygienic dispenser (e.g., 205) is malfunctioning or otherwise being falsely activated. The hub locations 190 can include location information about where the various dispensers (e.g., 205) are located throughout a healthcare facility such as a hospital. The accelerometer patterns 180 can include information about how the hygienic sensor adapter device 100 has been moved or tampered with. The infrared signals 182 can be detected by the active/passive infrared sensor 160 or the time of flight infrared sensor 165. The one or more images 184 can be gathered by the visible light camera 170. The usage information 195 stored in the storage device 198 can include the capacitive fluctuations 112, the hygiene event information 185, the operational behavior data 192, the hub locations 190, the RSSI patterns 175, the accelerometer patterns 180, the infrared signals 182, the one or more images 184, or the like. The usage information 195 stored in the storage device 198 can include a subject's location leading up to an event during an activation of the hygienic dispenser 205, a subject's location after an activation of the hygienic dispenser 205, a subject's orientation, hand hygiene compliance history of each subject, or the like.

The hygienic sensor adapter device 100 can be installed proximate to where a subject's hand 210 must present itself to activate the hygienic dispenser 205. The hygienic sensor adapter device 100 can detect a presence of a human hand 210 within an activation area 215 of the hygienic dispenser 205. It will be understood that the activation area 215 as illustrated in FIG. 2B is a schematic representation of an activation area, and an actual activation area can be larger, smaller, or shaped differently without departing from the inventive concepts disclosed herein.

The hygienic dispenser 205 can be table-mounted or wall-mounted. The hygienic dispenser 205 can dispense a hygienic substance such as soap, alcohol, lotion, a glove, a medication, or the like. The hygienic sensor adapter device 100 can be in the form of a drip-guard or drip-tray. It will be understood that a drip-guard or drip-tray need not be used or included. The hygienic sensor adapter device 100 can continuously or periodically gather samples to detect a human hand signal. In other words, the hygienic sensor adapter device 100 can detect a presence of a human hand (e.g., 210) within an activation area (e.g., 215) of the hygienic dispenser 205. A valid hand signal is a positive indication that a subject's human hand (e.g., 210) is likely to have activated the hygienic dispenser 205, is within a certain proximity to the hygienic dispenser 205, and/or is within a certain proximity to the hygienic sensor adapter device 100.

When the subject's hand 210 presents itself to activate the hygienic dispenser 205, the micro-controller unit 105 and the radio unit 115 of the hygienic sensor adapter device 100 can be activated, which can detect nearby badges (e.g., A through F) worn by different subjects (e.g., 1 through 6). In some embodiments, the badges (e.g., A through F) each include some form of wireless communication means such as Bluetooth, Bluetooth LE®, Zigbee®, NFC, or the like, to communicate with a corresponding wireless communication means (e.g., the one or more antennas 135 and/or the sensor 138) of the hygienic sensor adapter device 100. It will be understood that the term "badge" is not limited to any particularly shaped object, but rather, this is a broad term indicating an item that is worn by or is otherwise attached to a human subject. The human subjects can be, for example, healthcare workers 102 such as doctors, nurses, support staff, or the like.

The hygienic sensor adapter device 100 can gather received signal strength information (RSSI) patterns 175 associated with each badge (e.g., A through F) and associated subject (e.g., 1 through 6). In some embodiments, the radio unit 115 gathers the RSSI patterns 175.

For example, the RSSI-1 will be stronger than the RSSI-5 or RSSI-6, and therefore, the hygienic sensor adapter device 100 can determine that a subject (e.g., subject 1) having a badge that is associated with the RSSI-1 signal is closer in proximity to the hygienic sensor adapter device 100 than a subject (e.g., subject 5 or 6) having a badge that is associated with the RSSI-5 or RSSI-6. In some embodiments, the micro-controller unit 105 makes that determination. In an alternate embodiment, the hygienic sensor adapter device 100 transmits the RSSI patterns 175 to the remote cloud-based computer server 265, which makes that determination. For example, the hygienic sensor adapter device 100 can transmit the RSSI patterns 175 to the remote cloud-based computer server 265, which can determine that a subject (e.g., subject 1) having a badge that is associated with the RSSI-1 signal is closer in proximity to the hygienic sensor adapter device 100 than a subject (e.g., subject 5 or 6) having a badge that is associated with the RSSI-5 or RSSI-6. In this latter embodiment, the subject prediction logic section 270 of the remote cloud-based computer server 265 can determine the nearest subject to the hygienic sensor adapter device 100 without the hygienic sensor adapter device 100 needing to filter down the badges to only the closest threshold number of badges. In other words, the RSSI patterns 175 for all detected badges can be transmitted to the remote cloud-based computer server 265, which can then do the necessary processing to determine which of all of the detected badges is closest to the hygienic sensor adapter device 100, and consequently, to which subject the hand belongs that activated the hygienic dispenser 205. This allows the accuracy of subject determination to be greatly increased beyond that achievable based on RSSI data alone.

Dispenser activation 240 is as between a subject (e.g., subject 1) and the hygienic dispenser 205, whereas sensor device activation 245 is as between a subject (e.g., subject 1) and the hygienic sensor adapter device 100. In other words, a subject (e.g., subject 1) can cause the hygienic dispenser 205 and the sensor device activation 245 to be independently activated.

The hygienic sensor adapter device 100 can detect a threshold number of nearest badges. For example, the hygienic sensor adapter device 100 can detect the closest four badges (e.g., A, B, C, and D), as shown in FIG. 2A, or otherwise determine that those badges (e.g., A, B, C, and D) are the nearest to the hygienic sensor adapter device 100. In other words, the hygienic sensor adapter device 100 can detect all badges (e.g., A through F) that are dectable by the hygienic sensor adapter device 100, and then determine which among those badges (e.g., A through F) are the closest badges (e.g., A, B, C, and D). In some embodiments, the micro-controller unit 105 of the hygienic sensor adapter device 100 can determine which badges are the closest four badges to the hygienic sensor adapter device 100. It will be understood that the threshold number need not be four, but can be any positive integer number of closest badges.

The hygienic sensor adapter device 100 can transmit badge identifiers 260 for the closest found badges (e.g., A, B, C, and D) to a remote cloud-based computer server 265 connected to the cloud 215. The remote cloud-based computer server 265 can include subject prediction logic section 270. The subject prediction logic section 270 of the remote cloud-based computer server 265 can pick the badge and/or subject (e.g., badge A and/or subject 1) that is most likely to use the hygienic dispenser 205, or that is most likely to have used the hygienic dispenser 205 in the recent past. The hygienic sensor adapter device 100 can transmit additional usage information 195, such as the RSSI patterns 175, the accelerometer patterns 180, the infrared signals 182, the one or more images 184, the hygiene event information 185, the operational behavior data 192, the hub locations 190, and/or the capacitive fluctuations 112 to the remote cloud-based computer server 265. The remote cloud-based computer server 265 can include a false positive logic section 280.

The false positive logic section 280 can perform additional logic or checking on the usage information 195 to rule out false triggers, and to ensure that the most likely subject receives credit for the particular instance of dispenser use. The false positive logic section 280 can ensure that the hygienic dispenser 205 is not activating on its own, or that the hygienic sensor adapter device 100 is not activating on its own or otherwise producing false positives. For example, the false positive logic section 280 can analyze or check the operational behavior data 192 to verify that the hygienic dispenser 205 is operating normally and not producing false positives. Moreover, the remote cloud-based computer server 265 can include a capacitive fluctuation validation logic section 288, which can make a determination whether the measured capacitive fluctuations 112 indicate a valid hand signal.

One or more administrators can access the information on the remote cloud-based computer server 265 via the cloud 215 using one or more access devices such as a computer workstation 230, a laptop computer 225, a tablet 220, a smart phone 235, or the like. In some embodiments, the one or more administrators can adjust settings of the hygienic sensor adapter device 100 via the cloud 215. In some embodiments, the one or more access devices (e.g., 230, 225, 220, or 235) can provide control over the hygienic sensor system 200. In some embodiments, the one or more access devices (e.g., 230, 225, 220, or 235) can receive the data (e.g., 175, 180, 182, 184, 185, 192, 190, 112, and/or 260) directly from the hygienic sensor adapter device 100, process or store the data, and provide a determination directly back to the hygienic sensor adapter device 100 via the cloud 215. In some embodiments, a data-collection only hygienic sensor adapter device 100 can gather data regarding hand signals and subjects near the hygienic sensor adapter device 100, and send such information to the remote cloud-based computer server 265 via cloud 215, and/or to the access devices (e.g., 230, 225, 220, or 235).

Figure 2C:
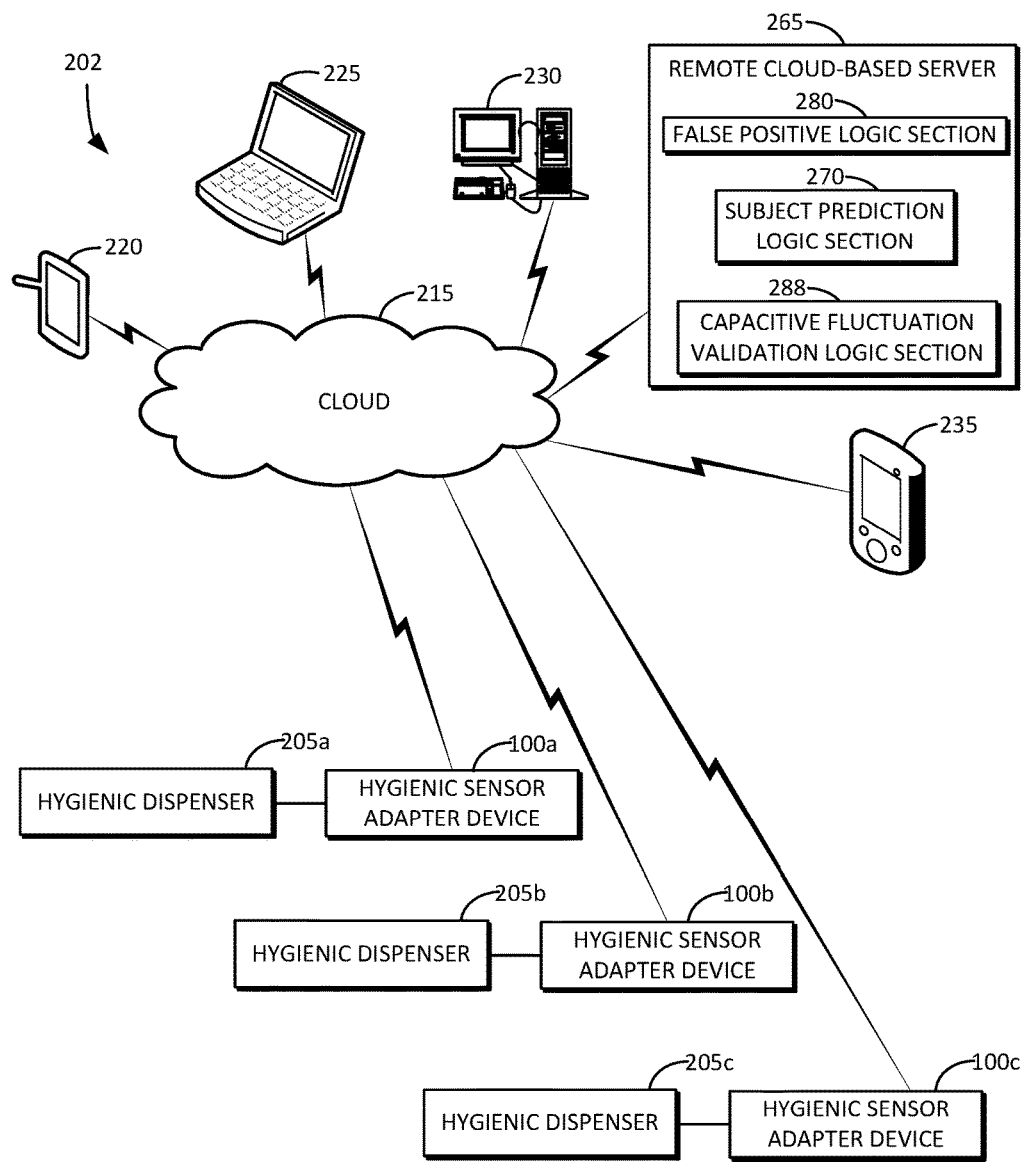
FIG. 2C illustrates a block diagram of an example hygienic sensor system including multiple hygienic sensor adapter devices and multiple corresponding hygienic dispensers in accordance with various embodiments of the present inventive concept.

FIG. 2C illustrates a block diagram of an example hygienic sensor system 202 including multiple hygienic sensor adapter devices (e.g., 100a, 100b, and 100c) and multiple corresponding hygienic dispensers (e.g., 205a, 205b, and 205c) in accordance with various embodiments of the present inventive concept. The remote cloud-based server 265 can be communicatively coupled via the cloud 215 to the each of the hygienic sensor adapter devices (e.g., 100a, 100b, and 100c). Each of the hygienic sensor adapter devices (e.g., 100a, 100b, and 100c) can be associated with a corresponding one of the hygienic dispensers (e.g., 205a, 205b, and 205c). Each of the hygienic sensor adapter devices (e.g., 100a, 100b, and 100c) and the corresponding hygienic dispensers (e.g., 205a, 205b, and 205c) can function in a manner the same as or similar to that described herein with respect to the hygienic sensor adapter device 100 and the hygienic dispenser 205. Therefore, a detailed description of that functionality is not repeated.

Figure 3:
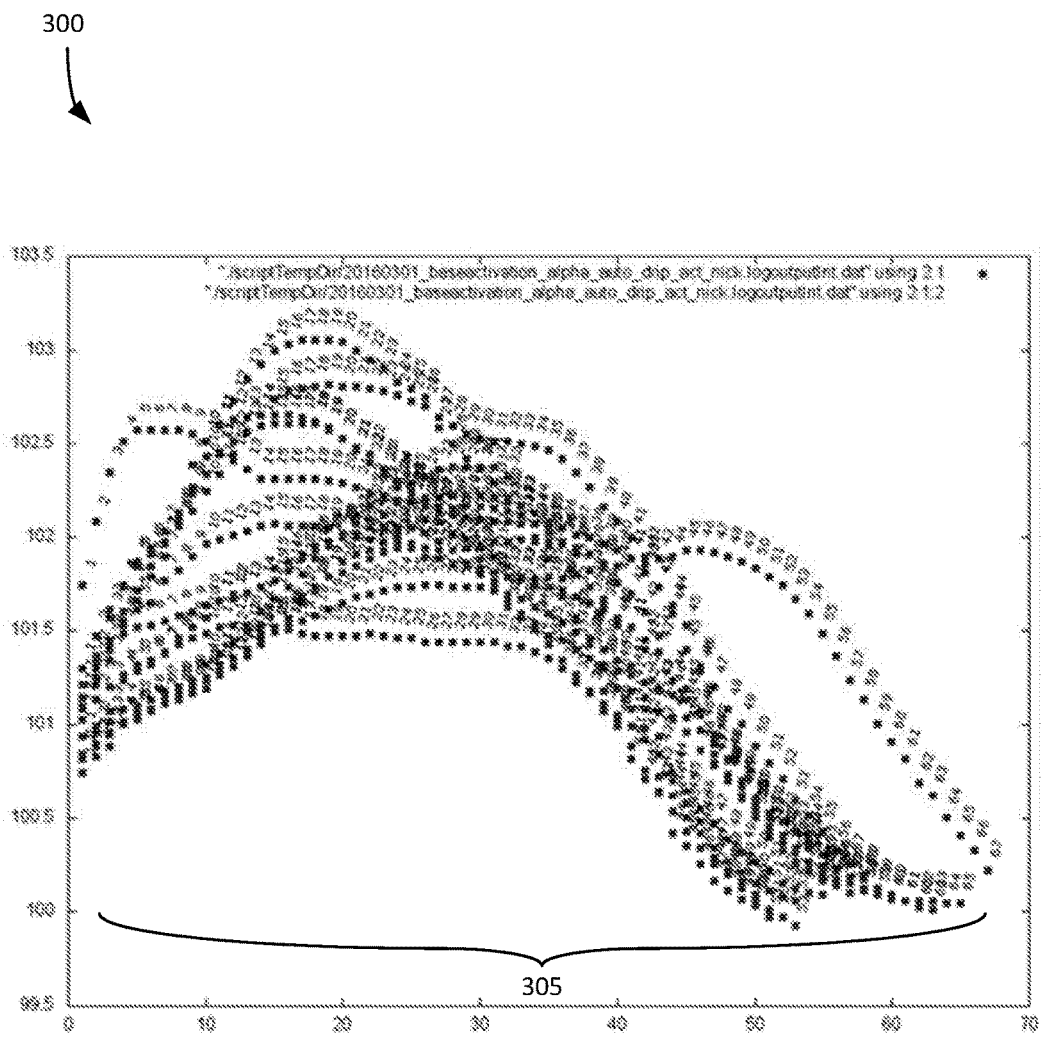
FIG. 3 illustrates a graph showing a valid hand activation signal based on a measured capacitance in accordance with various embodiments of the present inventive concept.

FIG. 3 illustrates a graph 300 showing a valid hand activation signal based on comparing predetermined valid capacitive fluctuations 315 with measured capacitive fluctuations 112 in accordance with various embodiments of the present inventive concept. Reference is now made to FIGS. 1 through 3.

The capacitive sensing electrodes 110 of the hygienic sensor adapter device 100 can sense or otherwise measure the capacitive fluctuations 112, and provide the gathered data to the micro-controller unit 105 and/or to the capacitive fluctuation validation logic section 188. The micro-controller unit 105 and/or the capacitive fluctuation validation logic section 188 can make a determination whether the measured capacitive fluctuations 112 indicate a valid hand signal. For example, the micro-controller unit 305 and/or the capacitive fluctuation validation logic section 188 can compare the predetermined valid capacitive fluctuations 315 with the measured capacitive fluctuations 112, and if within a certain tolerance, make the determination that the measured capacitive fluctuations 112 indicate a valid hand signal.

Alternatively or in addition, the micro-controller unit 105 can cause the gathered capacitive fluctuations 112 data to be transmitted to the remote cloud-based computer server 265 via the cloud 215 for the determination to be made remotely. In other words, the capacitive fluctuation validation logic section 288 of the remote cloud-based computer server 265 can determine whether the capacitive fluctuations 112 indicate a valid hand signal. For example, the capacitive fluctuation validation logic section 288 of the remote cloud-based computer server 265 can compare the predetermined valid capacitive fluctuations 315 with the measured capacitive fluctuations 112, and if within a certain tolerance, make the determination that the measured capacitive fluctuations 112 indicate a valid hand signal.

Figure 4:
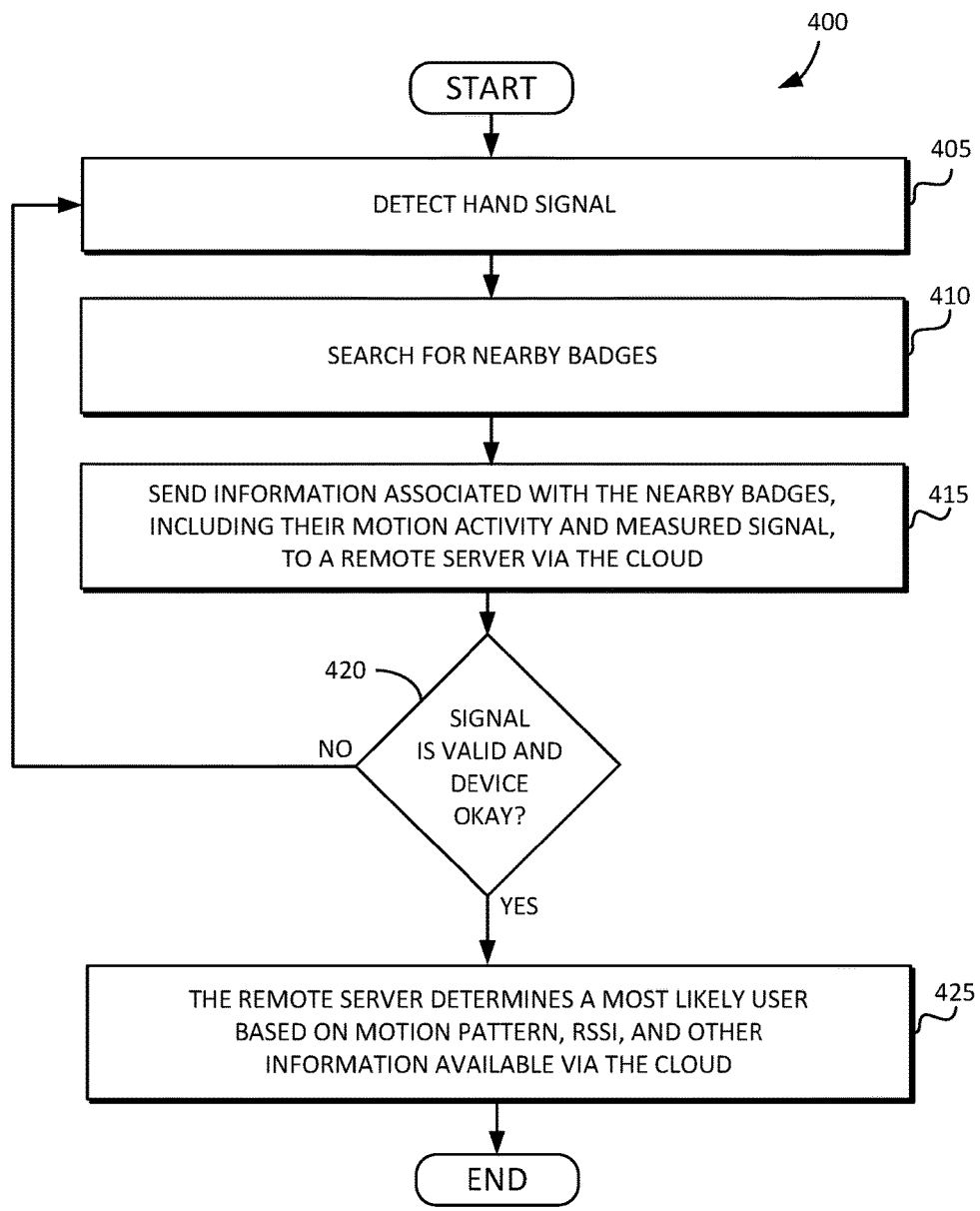
FIG. 4 illustrates a flow diagramming showing a technique for detecting a valid hand signal, searching nearby badges, and sending the gathered information to the cloud in accordance with various embodiments of the present inventive concept.

FIG. 4 illustrates a flow diagram 400 showing a technique for detecting a valid hand signal, searching nearby badges, and sending the gathered information to the cloud in accordance with various embodiments of the present inventive concept. The technique can begin at 405, where a hand signal can be detected by the hygienic sensor adapter device 100. At 410, the hygienic sensor adapter device 100 can search for nearby badges worn by various subjects. At 415, the hygienic sensor adapter device 100 can send information associated with the closest badges, such as the badge identifiers 260, and including their motion activity and measured signal data, to the remote cloud-based computer server (e.g., 265) via the cloud 215. For example, the information associated with the closest badges can include some or all of the usage information 195 such as the measured capacitive fluctuations 112, the hygiene event information 185, the hub locations 190, the RSSI patterns 175, or the like.

At 420, the remote cloud-based computer server (e.g., 265) can make a determination whether the hand signal is a valid hand signal, and whether the hygienic sensor adapter device 100 is functioning properly. If NO, the flow can return to 405 for further hand detection. Otherwise, if YES, the flow can proceed to 425. At 425, the remote cloud-based computer server (e.g., 265) can determine a most likely subject based on the hand motion pattern, the gathered RSSI information, and any additional data (e.g., 195) that may be available to the remote cloud-based computer server (e.g., 265) via the cloud 215, and that is useful in determining which is a most likely subject to be using the hand dispenser 205, such as: location of the dispenser 205 that was used, subject's location leading up to the event, during and after the activation, subject's orientation, subject's hand hygiene compliance leading up to activation, and the like.

Figure 5:
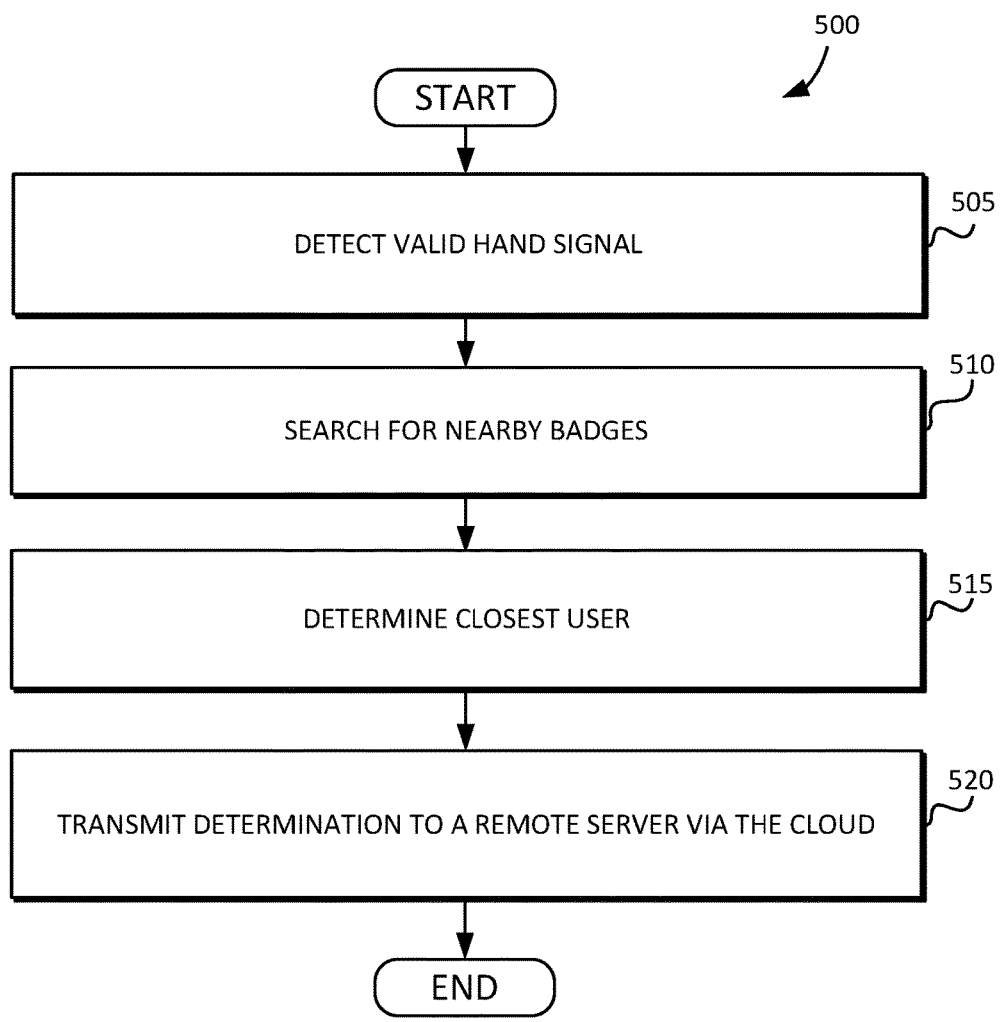
FIG. 5 illustrates a flow diagramming showing a technique for detecting a valid hand signal, searching nearby badges, making a determination, and sending the determination to the cloud in accordance with various embodiments of the present inventive concept.

FIG. 5 illustrates a flow diagram 500 showing a technique for detecting a valid hand signal, searching nearby badges, making a determination, and sending the determination to the a remote cloud-based computer server via the cloud in accordance with various embodiments of the present inventive concept. The technique can begin at 505, where a hand signal can be detected by the hygienic sensor adapter device 100. At 510, the hygienic sensor adapter device 100 can search for nearby badges (e.g., A through F) associated with corresponding subjects (e.g., subjects 1 through 6). At 515, the hygienic sensor adapter device 100 can make a determination of the closest subject from among the multiple subjects. At 520, the hygienic sensor adapter device 100 can transmit the determination to the remote cloud-based computer server (e.g., 265) via the cloud 215.

Reference is now made to FIGS. 1 through 5.

In some embodiments, a system 200 for monitoring hygienic dispenser usage and compliance is disclosed. The system 200 can include a hygienic dispenser 205 configured to dispense a hygienic substance, such as sanitizer, soap, a glove, or the like. The system 200 can include a hygienic sensor adapter device 100 proximately disposed to the hygienic dispenser 205. In some embodiments, the hygienic sensor adapter device 100 is configured to detect a presence of a human hand 210 within an activation area 215 of the hygienic dispenser 205. In some embodiments, the hygienic sensor adapter device 100 includes a sensor 138 configured to detect one or more badges (e.g., A through F) worn by corresponding one or more human subjects (e.g., 1 through 6).

The system 200 can further include a remote cloud-based computer server 265 including a subject prediction logic section 270 configured to determine a particular human subject (e.g., subject 1) from among the one or more human subjects (e.g., 1 through 6) to which the human hand 210 belongs. In some embodiments, the one or more human subjects include a plurality of human subjects (e.g., 1 through 6) each wearing a badge (e.g., A through F).

In some embodiments, the hygienic sensor adapter device 100 includes a radio unit 115 including the sensor 138 that is configured to detect each of the badges (e.g., A through F) worn by the plurality of human subjects (e.g., 1 through 6).

In some embodiments, the hygienic sensor adapter device 100 includes a micro-controller unit 105 configured to determine a threshold number (e.g., 4) of nearest badges (e.g., badges A, B, C and D) from among the detected badges (e.g., A through F) worn by the plurality of human subjects (e.g., 1 through 6). In some embodiments, the radio unit 115 of the hygienic sensor adapter device 100 includes an antenna 135 that is configured to wirelessly transmit badge identifiers 260 for the threshold number (e.g., 4) of the nearest badges (e.g., badges A, B, C and D) to the remote cloud-based computer server 265.

In some embodiments, the subject prediction logic section 270 of the remote cloud-based computer server 265 is configured to determine the particular human subject (e.g., subject 1) from among the plurality of human subjects (e.g., 1 through 6) to which the human hand 210 belongs based on the badge identifiers 260 for the threshold number (e.g., 4) of the nearest badges (e.g., badges A, B, C and D).

In some embodiments, the radio unit 115 is configured to sense one or more received signal strength information (RSSI) patterns 175. In some embodiments, the micro-controller unit 105 is configured to determine the threshold number (e.g., 4) of the nearest badges (e.g., badges A, B, C and D) from among the detected badges (e.g., A through F) worn by the plurality of human subjects (e.g., 1 through 6) based on the RSSI patterns 175.

In some embodiments, the one or more human subjects include a plurality of human subjects (e.g., 1 through 6) each wearing a badge (e.g., A through F). In some embodiments, the hygienic sensor adapter device 100 includes a radio unit 135 having the sensor 138 that is configured to detect each of the badges (e.g., A through F) worn by the plurality of human subjects (e.g., 1 through 6). In some embodiments, the radio unit 115 of the hygienic sensor adapter device 100 includes an antenna 135 that is configured to wirelessly transmit badge identifiers 260 for all of the detected badges (e.g., A through F) to the remote cloud-based computer server 265.

In some embodiments, the subject prediction logic section 270 of the remote cloud-based computer server 265 is configured to determine the particular human subject (e.g., subject 1) from among the plurality of human subjects (e.g., 1 through 6) to which the human hand 210 belongs based on the badge identifiers 260 for all of the detected badges (e.g., A through F).

In some embodiments, the radio unit 115 is configured to sense one or more received signal strength information (RSSI) patterns 175, and to wirelessly transmit the one or more RSSI patterns 175 to the remote cloud-based computer server 265. In some embodiments, the subject prediction logic section 270 of the remote cloud-based computer server 265 is configured to determine the particular human subject (e.g., subject 1) from among the plurality of human subjects (e.g., 1 through 6) to which the human hand 210 belongs based on the RSSI patterns 175.

In some embodiments, the hygienic sensor adapter device 100 includes a capacitive fluctuation validation logic section 188 that is configured to receive and interpret capacitive fluctuations 112 detected by capacitive sensing electrodes 110 due to the presence of the human hand 210 within the activation area 215 of the hygienic dispenser 205. In some embodiments, the hygienic sensor adapter device 100 is configured to at least one of (i) store the capacitive fluctuations 112 in a storage device 198 of the hygienic sensor adapter device 100 or (ii) transmit the capacitive fluctuations 112 to the remote cloud-based computer server 265. In some embodiments, the remote cloud-based computer server 265 includes a capacitive fluctuation validation logic section 288 that is configured to receive and interpret the capacitive fluctuations 112 due to the presence of the human hand 210 within the activation area 215 of the hygienic dispenser 205.

In some embodiments, the capacitive fluctuation validation logic section (e.g., 188 or 288) of at least one of (i) the hygienic sensor adapter device 100 or (ii) the remote cloud-based computer server 265 is configured to compare the capacitive fluctuations 112 to predetermined valid capacitive fluctuations 305 to determine whether the capacitive fluctuations 112 indicate a valid hand signal.

In some embodiments, the hygienic sensor adapter device 100 includes an infrared sensor (e.g., 160 or 165) configured to detect infrared signals 182. In some embodiments, the hygienic sensor adapter device 100 includes a visible light camera 170 configured to gather one or more images 184. In some embodiments, the hygienic sensor adapter device 100 is configured to at least one of (i) store the infrared signals 182 and the one or more images 184 in a storage device 198 of the hygienic sensor adapter device 100 or (ii) transmit the infrared signals 182 and the one or more images 184 to the remote cloud-based computer server 265.

In some embodiments, the subject prediction logic section 270 of the remote cloud-based computer server 265 is configured to determine the particular human subject (e.g., subject 1) from among the plurality of human subjects (e.g., subjects 1 through 6) to which the human hand 210 belongs based on at least one of (i) the infrared signals 182 or (ii) the one or more images 184.

In some embodiments, the remote cloud-based computer server 265 further comprises a false positive logic section 280 that is configured to perform checking of operational behavior data (e.g., 192) associated with the hygienic dispenser 205 to rule out false positive activations thereof.

In some embodiments, the system 202 includes a plurality of hygienic dispensers (e.g., 205a, 205b, and 205c) including the hygienic dispenser (e.g., 205), each of the plurality of hygienic dispensers being configured to dispense the hygienic substance. In some embodiments, the system 202 includes a plurality of hygienic sensor adapter devices (e.g., 100a, 100b, and 100c) including the hygienic sensor adapter device (e.g., 100), each of the plurality of hygienic sensor adapter devices (e.g., 100a, 100b, and 100c) being proximately disposed to a corresponding one of the hygienic dispensers (e.g., 205a, 205b, and 205c). In some embodiments, the hygienic sensor adapter devices (e.g., 100a, 100b, and 100c) are each configured to detect the presence of the human hand 210 within a corresponding activation area (e.g., 215) of the corresponding hygienic dispenser (e.g., 205a, 205b, and 205c). In other words, each hygienic dispenser has its own activation area. In some embodiments, each of the hygienic sensor adapter devices 100 includes a corresponding sensor (e.g., 138) configured to detect the one or more badges (e.g., A through F) worn by the corresponding one or more human subjects (e.g., subjects 1 through 6). In some embodiments, the remote cloud-based computer server 265 is communicatively coupled to the plurality of hygienic sensor adapter devices (e.g., 205a, 205b, and 205c).

In some embodiments, the hygienic sensor adapter device 100 further comprises a display screen 125 configured to show a visual indication 150 about at least one of (i) a status or (ii) an operation of the hygienic sensor adapter device 100. In some embodiments, the hygienic sensor adapter device 100 includes a storage device 198. In some embodiments, the hygienic sensor adapter device 100 is configured to store hygiene event information 185 associated with hand activations of the hygienic dispenser 205 in the storage device 198. In some embodiments, the hygiene event information includes instances in which each subject (e.g., subjects 1 through 6) from among the one or more human subjects used the hygienic dispenser 205.

In some embodiments, the hygienic sensor adapter device 100 includes a storage device 198. In some embodiments, the hygienic sensor adapter device 100 is configured to store a hub location 190 of the hygienic sensor adapter device 100 within a healthcare facility in the storage device 198. In some embodiments, the hygienic sensor adapter device 100 includes an accelerometer 155 configured to detect at least one of (i) movement of the hygienic sensor adapter device 100 or (ii) tampering with the hygienic sensor adapter device 100.

In some embodiments, the hygienic sensor adapter device 100 is configured to catch the hygienic substance, and is in the form of at least one of (i) a drip guard or (ii) a drip tray.

Embodiments are described herein, and illustrated in the drawings, in terms of functional blocks, units and/or modules. Those skilled in the art will appreciate that these blocks, units and/or modules can be physically implemented by electronic (or optical) circuits such as logic circuits, discrete components, microprocessors, hard-wired circuits, memory elements, wiring connections, and the like, which may be formed using semiconductor-based fabrication techniques or other manufacturing technologies. In the case of the blocks, units and/or modules being implemented by microprocessors or similar, they may be programmed using software (e.g., microcode) to perform various functions discussed herein and may optionally be driven by firmware and/or software. Alternatively, each block, unit and/or module may be implemented by dedicated hardware, or as a combination of dedicated hardware to perform some functions and a processor (e.g., one or more programmed microprocessors and associated circuitry) to perform other functions. Also, each block, unit and/or module of the embodiments may be physically separated into two or more interacting and discrete blocks, units and/or modules without departing from the scope of the inventive concepts. Further, the blocks, units and/or modules of the embodiments may be physically combined into more complex blocks, units and/or modules without departing from the scope of the inventive concepts.

The following discussion is intended to provide a brief, general description of a suitable machine or machines in which certain aspects of the inventive concept can be implemented. Typically, the machine or machines include a system bus to which is attached processors, memory, e.g., random access memory (RAM), read-only memory (ROM), or other state preserving medium, storage devices, a video interface, and input/output interface ports. The machine or machines can be controlled, at least in part, by input from conventional input devices, such as keyboards, mice, etc., as well as by directives received from another machine, interaction with a virtual reality (VR) environment, biometric feedback, or other input signal. As used herein, the term "machine" is intended to broadly encompass a single machine, a virtual machine, or a system of communicatively coupled machines, virtual machines, or devices operating together. Exemplary machines include computing devices such as personal computers, workstations, servers, portable computers, handheld devices, telephones, tablets, etc., as well as transportation devices, such as private or public transportation, e.g., automobiles, trains, cabs, etc.

The machine or machines can include embedded controllers, such as programmable or non-programmable logic devices or arrays, Application Specific Integrated Circuits (ASICs), embedded computers, smart cards, and the like. The machine or machines can utilize one or more connections to one or more remote machines, such as through a network interface, modem, or other communicative coupling. Machines can be interconnected by way of a physical and/or logical network, such as an intranet, the Internet, local area networks, wide area networks, etc. One skilled in the art will appreciate that network communication can utilize various wired and/or wireless short range or long range carriers and protocols, including radio frequency (RF), satellite, microwave, Institute of Electrical and Electronics Engineers (IEEE) 545.11, Bluetooth®, optical, infrared, cable, laser, etc.

Embodiments of the inventive concept can be described by reference to or in conjunction with associated data including functions, procedures, data structures, application programs, etc. which when accessed by a machine results in the machine performing tasks or defining abstract data types or low-level hardware contexts. Associated data can be stored in, for example, the volatile and/or non-volatile memory, e.g., RAM, ROM, etc., or in other storage devices and their associated storage media, including hard-drives, floppy-disks, optical storage, tapes, flash memory, memory sticks, digital video disks, biological storage, etc. Associated data can be delivered over transmission environments, including the physical and/or logical network, in the form of packets, serial data, parallel data, propagated signals, etc., and can be used in a compressed or encrypted format. Associated data can be used in a distributed environment, and stored locally and/or remotely for machine access.

Having described and illustrated the principles of the inventive concept with reference to illustrated embodiments, it will be recognized that the illustrated embodiments can be modified in arrangement and detail without departing from such principles, and can be combined in any desired manner And although the foregoing discussion has focused on particular embodiments, other configurations are contemplated. In particular, even though expressions such as "according to an embodiment of the invention" or the like are used herein, these phrases are meant to generally reference embodiment possibilities, and are not intended to limit the inventive concept to particular embodiment configurations. As used herein, these terms can reference the same or different embodiments that are combinable into other embodiments.

Embodiments of the invention may include a non-transitory machine-readable medium comprising instructions executable by one or more processors, the instructions comprising instructions to perform the elements of the embodiments as described herein.

Consequently, in view of the wide variety of permutations to the embodiments described herein, this detailed description and accompanying material is intended to be illustrative only, and should not be taken as limiting the scope of the inventive concept. What is claimed as the invention, therefore, is all such modifications as may come within the scope and spirit of the following claims and equivalents thereto.

The invention claimed is:

1. A system for monitoring hygienic dispenser usage and compliance, the system comprising:
    a hygienic dispenser configured to dispense a hygienic substance;
    a hygienic sensor adapter device proximately disposed to the hygienic dispenser, wherein the hygienic sensor adapter device is configured to detect a presence of a human hand within an activation area of the hygienic dispenser, and wherein the hygienic sensor adapter device includes a radio unit configured to detect one or more badges worn by corresponding one or more human subjects; and
    a remote cloud-based computer server including a subject prediction logic section configured to determine a particular human subject from among the one or more human subjects to which the human hand belongs;
wherein:
    the hygienic sensor adapter device includes a capacitive fluctuation validation logic section that is configured to receive and interpret capacitive fluctuations due to the presence of the human hand within the activation area of the hygienic dispenser; and
    the hygienic sensor adapter device is configured to at least one of (i) store the capacitive fluctuations in a storage device of the hygienic sensor adapter device or (ii) transmit the capacitive fluctuations to the remote cloud-based computer server.

2. The system of claim 1, wherein:
    the one or more human subjects each wearing a badge;
    the hygienic sensor adapter device includes a micro-controller unit configured to determine a threshold number of nearest badges from among the one or more badges worn by the corresponding one or more human subjects;
    the radio unit of the hygienic sensor adapter device includes an antenna that is configured to wirelessly transmit badge identifiers for the threshold number of the nearest badges to the remote cloud-based computer server; and
    the subject prediction logic section of the remote cloud-based computer server is configured to determine the particular human subject from among the one or more human subjects to which the human hand belongs based on the badge identifiers for the threshold number of the nearest badges.

3. The system of claim 2, wherein:
    the radio unit is configured to sense one or more received signal strength information (RSSI) patterns; and
    the micro-controller unit is configured to determine the threshold number of the nearest badges from among the one or more badges worn by the corresponding one or more human subjects based on the RSSI patterns.

4. The system of claim 1, wherein:
    the one or more human subjects each wearing a badge;
    the radio unit of the hygienic sensor adapter device includes an antenna that is configured to wirelessly transmit badge identifiers for all of the one or more badges to the remote cloud-based computer server; and
    the subject prediction logic section of the remote cloud-based computer server is configured to determine the particular human subject from among the one or more human subjects to which the human hand belongs based on the badge identifiers for all of the one or more badges.

5. The system of claim 4, wherein:
    the radio unit is configured to sense one or more received signal strength information (RSSI) patterns, and to wirelessly transmit the one or more RSSI patterns to the remote cloud-based computer server; and
    the subject prediction logic section of the remote cloud-based computer server is configured to determine the particular human subject from among the one or more human subjects to which the human hand belongs based on the RSSI patterns.

6. The system of claim 1, wherein the remote cloud-based computer server includes a capacitive fluctuation validation logic section that is configured to receive and interpret the capacitive fluctuations due to the presence of the human hand within the activation area of the hygienic dispenser.

7. The system of claim 1, wherein the capacitive fluctuation validation logic section of at least one of (i) the hygienic sensor adapter device or (ii) the remote cloud-based computer server is configured to compare the capacitive fluctuations to predetermined valid capacitive fluctuations to determine whether the capacitive fluctuations indicate a valid hand signal.

8. The system of claim 1, wherein:
the hygienic sensor adapter device includes an infrared sensor configured to detect infrared signals;
the hygienic sensor adapter device includes a visible light camera configured to gather one or more images; and
the hygienic sensor adapter device is configured to at least one of (i) store the infrared signals and the one or more images in the storage device of the hygienic sensor adapter device or (ii) transmit the infrared signals and the one or more images to the remote cloud-based computer server.

9. The system of claim 8, wherein the subject prediction logic section of the remote cloud-based computer server is configured to determine the particular human subject from among the one or more human subjects to which the human hand belongs based on at least one of (i) the infrared signals or (ii) the one or more images.

10. The system of claim 1, further comprising:
a plurality of hygienic dispensers including the hygienic dispenser, each of the plurality of hygienic dispensers being configured to dispense the hygienic substance;
a plurality of hygienic sensor adapter devices including the hygienic sensor adapter device, each of the plurality of hygienic sensor adapter devices being proximately disposed to a corresponding one of the hygienic dispensers, wherein the plurality of hygienic sensor adapter devices are each configured to detect a presence of a human hand within an activation area of the corresponding one of the plurality of hygienic dispensers, and wherein each of the plurality of hygienic sensor adapter devices includes a corresponding radio unit configured to detect the one or more badges worn by the corresponding one or more human subjects; and
the remote cloud-based computer server is communicatively coupled to the plurality of hygienic sensor adapter devices.

11. The system of claim 1, wherein the hygienic sensor adapter device further comprises a display screen configured to show a visual indication about at least one of (i) a status or (ii) an operation of the hygienic sensor adapter device.

12. The system of claim 1, wherein:
the hygienic sensor adapter device is configured to store hygiene event information associated with hand activations of the hygienic dispenser in the storage device; and
the hygiene event information includes instances in which each subject from among the one or more human subjects used the hygienic dispenser.

13. The system of claim 1, wherein:
the hygienic sensor adapter device is configured to store a hub location of the hygienic sensor adapter device within a healthcare facility in the storage device.

14. The system of claim 1, wherein the hygienic sensor adapter device includes an accelerometer configured to detect at least one of (i) movement of the hygienic sensor adapter device or (ii) tampering with the hygienic sensor adapter device.

15. The system of claim 1, wherein the hygienic sensor adapter device is configured to catch the hygienic substance, and is in the form of at least one of (i) a drip guard or (ii) a drip tray.

16. A system for monitoring hygienic dispenser usage and compliance, the system comprising:
a hygienic dispenser configured to dispense a hygienic substance;
a hygienic sensor adapter device proximately disposed to the hygienic dispenser, wherein the hygienic sensor adapter device is configured to detect a presence of a human hand within an activation area of the hygienic dispenser, and wherein the hygienic sensor adapter device includes a radio unit configured to detect one or more badges worn by corresponding one or more human subjects; and
a remote cloud-based computer server including a subject prediction logic section configured to determine a particular human subject from among the one or more human subjects to which the human hand belongs;
wherein the remote cloud-based computer server further comprises a false positive logic section that is configured to perform checking of operational behavior data associated with the hygienic dispenser to rule out false positive activations thereof.

* * * * *